United States Patent
Richter

(10) Patent No.: US 8,486,130 B2
(45) Date of Patent: Jul. 16, 2013

(54) TWO BALLOON STAGED STENT EXPANSION

(75) Inventor: Jacob Richter, Arsuf (IL)

(73) Assignee: Medinol Ltd., Tel Aviv (IL)

( * ) Notice: Subject to any disclaimer, the term of this patent is extended or adjusted under 35 U.S.C. 154(b) by 1184 days.

(21) Appl. No.: 11/371,714

(22) Filed: Mar. 8, 2006

(65) Prior Publication Data
US 2006/0173526 A1    Aug. 3, 2006

Related U.S. Application Data

(62) Division of application No. 09/878,749, filed on Jun. 11, 2001, now Pat. No. 7,052,510.

(60) Provisional application No. 60/211,642, filed on Jun. 14, 2000.

(51) Int. Cl.
*A61F 2/06*    (2006.01)

(52) U.S. Cl.
USPC ............................................. 623/1.11

(58) Field of Classification Search
USPC ............ 604/96.01, 101.01, 101.02; 623/1.11
See application file for complete search history.

(56) References Cited

U.S. PATENT DOCUMENTS

| | | | |
|---|---|---|---|
| 4,744,366 A | 5/1988 | Jang | |
| 5,242,399 A * | 9/1993 | Lau et al. | 604/104 |
| 5,342,305 A | 8/1994 | Shonk | |
| 5,358,487 A * | 10/1994 | Miller | 604/103.11 |
| 5,447,497 A * | 9/1995 | Sogard et al. | 604/101.02 |
| 5,653,689 A | 8/1997 | Buelna et al. | |
| 5,704,913 A | 1/1998 | Abele et al. | |
| 5,749,851 A * | 5/1998 | Wang | 604/96.01 |
| 5,876,376 A | 3/1999 | Schwab et al. | |
| 6,136,011 A | 10/2000 | Stambaugh | |
| 6,419,685 B2 | 7/2002 | Di Caprio et al. | |
| 6,605,056 B2 | 8/2003 | Eidenschink et al. | |
| 6,881,216 B2 * | 4/2005 | Di Caprio et al. | 606/192 |
| 7,052,510 B1 * | 5/2006 | Richter | 623/1.11 |

FOREIGN PATENT DOCUMENTS

| | | |
|---|---|---|
| EP | 0 903 121 A1 | 3/1999 |
| JP | 10-314297 | 12/1998 |
| WO | 96/38109 | 12/1996 |
| WO | 99/12601 | 3/1999 |
| WO | 00/03662 | 1/2000 |

OTHER PUBLICATIONS

International Search Report for International Application No. PCT/IL01/00543.

(Continued)

*Primary Examiner* — Gregory Anderson
(74) *Attorney, Agent, or Firm* — Cadwalader, Wickersham & Taft LLP

(57) ABSTRACT

A catheter with two balloons for implanting a stent without flaring at the ends of the stent during implantation has an outer balloon overlying an inner balloon. The length of the inner balloon is shorter than the length of the outer balloon and shorter than a stent which is mounted over both balloons. Upon inflation of the inner balloon, the inner balloon expands only the center of the stent. After the center of the stent is expanded, further application of pressure bursts the inner balloon allowing application of pressure to the outer balloon. The outer balloon is then inflated, expanding the ends of the stent.

8 Claims, 3 Drawing Sheets

OTHER PUBLICATIONS

Office Actions, Responses to Office Actions and Notice of Allowance for related U.S. Appl. No. 09/878,749, issued as U.S. Patent No. 7,052,510: • Examiner Interview Summary and Corrected Notice of Allowance dated May 4, 2006 • Notice of Allowance dated Jan. 3, 2006 • Applicant's Appeal Brief dated Oct. 14, 2005 • Advisory Action dated Jun. 28, 2005 • Amendment and Response to Final Office Action dated Jun. 2, 2005 • Final Office Action dated Apr. 20, 2005 • Amendment and Response to Non-Final Office Action dated Feb. 17, 2005 • Non-Final Office Action dated Jan. 11, 2005.

* cited by examiner

TWO BALLOON STAGED STENT EXPANSION

CROSS-REFERENCE TO RELATED APPLICATIONS

This application is a divisional of U.S. patent application Ser. No. 09/878,749 filed on Jun. 11, 2001, issued as U.S. Pat. No. 7,052,510 which is a non-provisional of U.S. provisional application Ser. No. 60/211,642 filed on Jun. 14, 2000.

FIELD OF THE INVENTION

The present invention relates generally to catheter balloons for implanting stents. More particularly, the present invention relates to a catheter balloon which utilizes two balloons coaxially disposed within one another.

BACKGROUND OF THE INVENTION

It is well known to use a balloon catheter to intraluminally deliver and implant a stent. Typically, to implant a stent with a balloon catheter, the unexpanded stent is disposed around the deflated balloon of a balloon catheter. The balloon is then delivered to the desired implantation site and inflated. The inflation of the balloon expands the stent, implanting it at the desired location.

One shortcoming of conventional balloon catheters is that they may cause the ends of the stent to flare out during implantation. This flaring out is referred to as "dogboning". Dogboning causes at least two undesirable effects. First, dogboning exacerbates any foreshortening of the stent during expansion. Second, dogboning causes the edges of the end of the stent to project in a direction perpendicular to the wall of the vessel in which the stent is being implanted. These projecting edges potentially increase trauma to the wall of the lumen.

SUMMARY OF THE INVENTION

Embodiments of the present invention include a balloon catheter with two balloons is disclosed. An inner balloon is shorter than an outer balloon, and also shorter than a stent which is to be implanted. The outer balloon overlays the inner balloon, and is longer that the stent.

To implant the stent, the catheter is delivered to a desired site in a vessel. Pressure is applied to the inner balloon, inflating the balloon and implanting the central portion of the stent. Further increases in pressure rupture the inner balloon. Because the outer balloon overlays the inner balloon, the pressure inflates the outer balloon, expanding the remainder of the stent. The balloons may then be deflated and removed, leaving the implanted stent in the vessel.

DETAILED DESCRIPTION OF THE INVENTION

Figure 1:
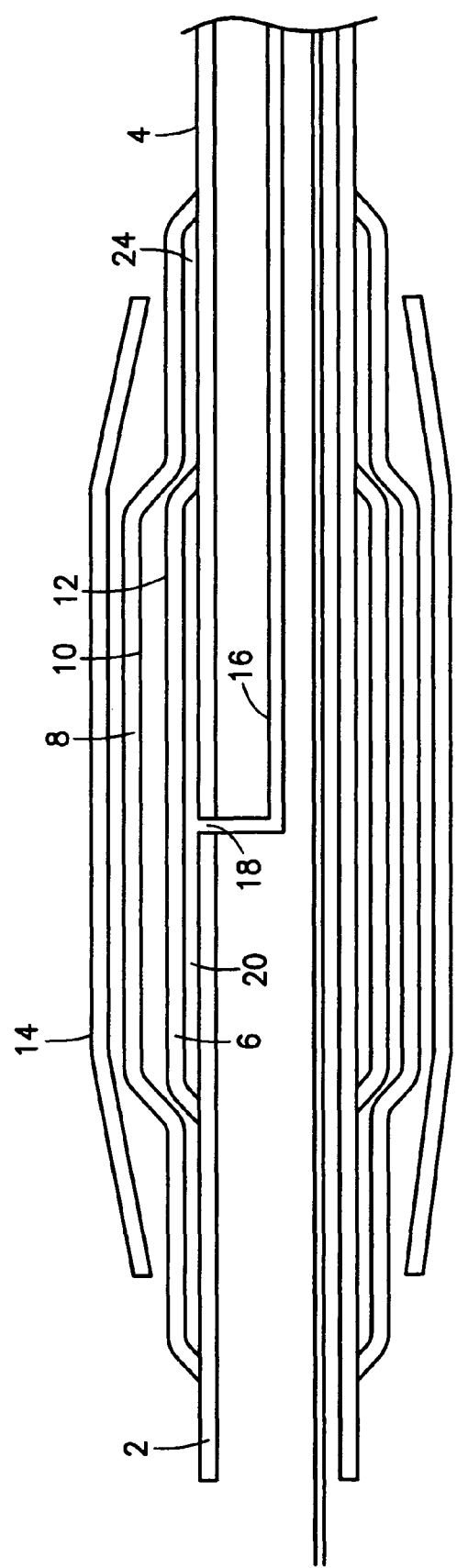
FIG. 1 shows a cross-sectional view of an embodiment of a catheter balloon assembly constructed according to the principles of the present invention which is in the deflated condition.

FIG. 1 shows a schematic view of an embodiment of a catheter balloon constructed in accordance with the principles of the present invention. The details of the catheter have not been included here, as they are well known to those skilled in the art. The precise configurations of the catheter shaft, guidewire lumen, and inflation lumen can be chosen as desired. For example, the catheter may be designed as a rapid-exchange system or as an over-the-wire system. The balloon catheter includes a catheter shaft 2. An inner balloon 6 is sealed to the outer surface 4 of the catheter shaft 2. The length of the inner balloon is chosen so that it is less than the length of the stent which it is designed to implant. The inner balloon 6 may be formed of a non-compliant material.

An outer balloon 8 is disposed around the inner balloon 6. The inner surface 10 of the outer balloon is immediately adjacent to the outer surface of the inner balloon. The two surfaces are permitted to move with respect to each other. The outer balloon 8 is sealed to the outer surface 4 of the catheter shaft 2 at the ends of the balloon. The outer balloon 8 may be formed of a non-compliant material. In the illustrated embodiment, the length of the outer balloon is chosen so that it is approximately 4 mm longer than the stent. In this and other embodiments, when the stent is crimped around the deflated balloon, the same amount of balloon may extend past the stent on each side—i.e. the balloon may, for example, extend past the stent by 2 mm on each side.

An inflation lumen 16 is located within the catheter shaft 4. The inflation lumen 16 is in fluid communication with the interior 20 of the inner balloon 6 through an aperture 18 in the catheter shaft 4. A pressurized medium, such as saline, may be introduced into the inflation lumen 16 to inflate the inner balloon. The space between the inner balloon and the outer balloon is not provided with an inflation lumen.

Figure 2:
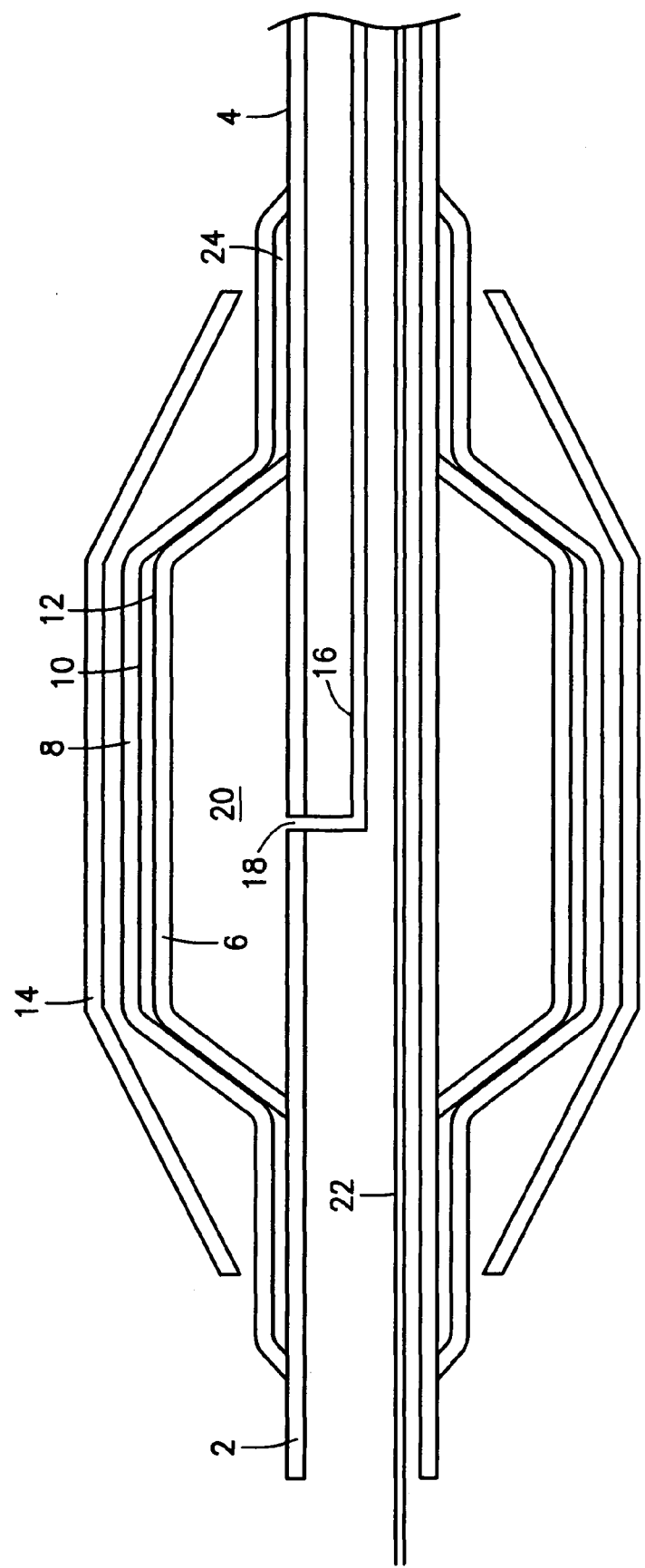
FIG. 2 shows a cross-sectional view of the catheter of FIG. 1 after partial inflation.

In operation, a guidewire 22 may be routed to the desired inflation location. The balloon catheter, the catheter shaft 4 of which has a guidewire port located adjacent the balloons, with a crimped stent may be then placed over the guidewire 22 and delivered to the desired location. A pressurized medium is introduced into the inflation lumen. The pressurized medium passes into the interior 20 of the inner balloon 6, and begins to inflate the inner balloon 6. The inner balloon 6 applies pressure to both the stent 14 and the outer balloon 8. Typically, at approximately 3 or 4 atmospheres (depending on the particular stent design chosen), the stent 14 begins to expand. As shown in FIG. 2, because the inner balloon 6 is shorter than the stent 14, only the middle portion of the stent 14 begins to expand. At, for example, approximately five atmospheres, the stent 14 is sufficiently expanded so that it is implanted into the vessel wall.

Figure 3:
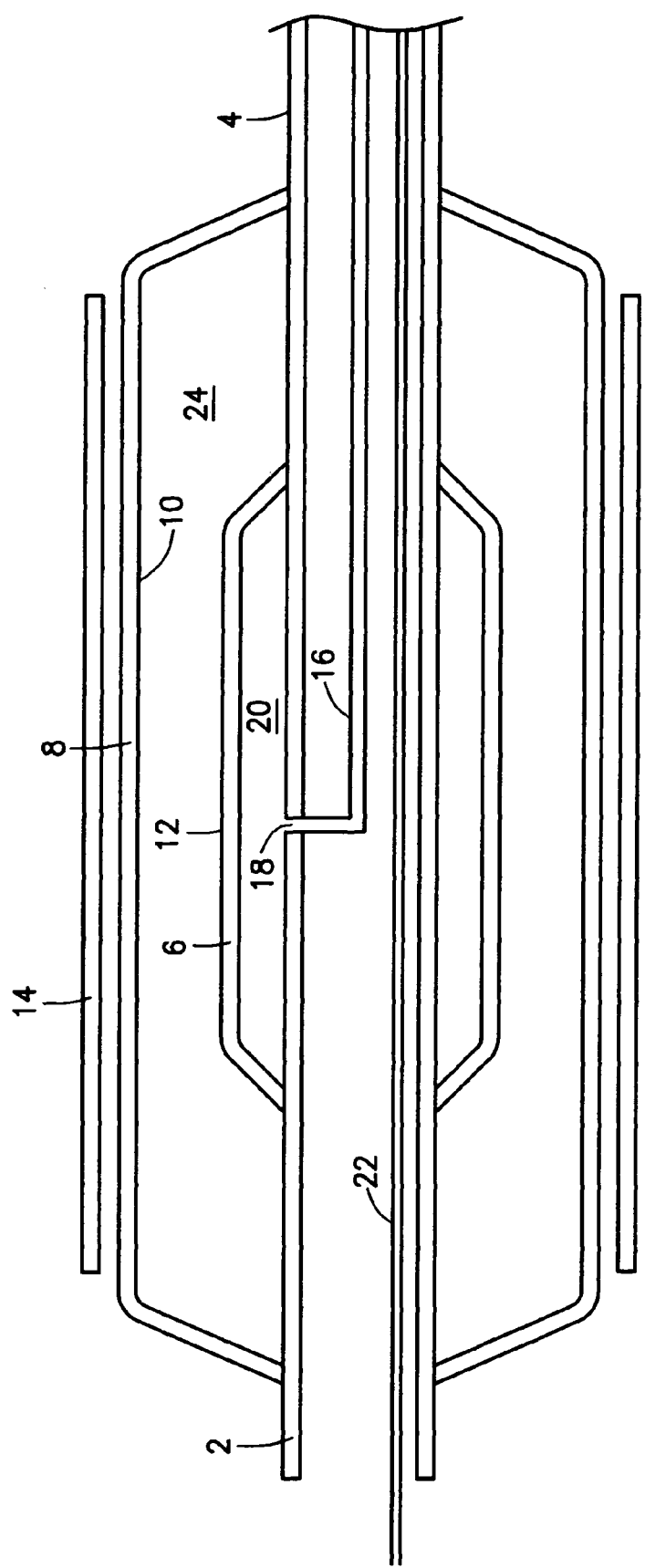
FIG. 3 shows a cross-sectional view of the catheter of FIG. 1 after full inflation.

As shown in FIG. 3, upon further application of the pressurized medium to the inflation lumen, the inner balloon 6 ruptures. The burst pressure of the inner balloon may be less than 10 atmospheres, and in some embodiments be approximately 5 atmospheres, for example. Rupture of the inner balloon 6 allows fluid communication between the inflation lumen 16 and the cavity formed between the outer balloon and the inner balloon.

When further pressure is applied to the inflation lumen, the outer balloon expands the entire length of the stent. The operator may then apply as much pressure as desired, up to the burst pressure of the outer balloon to firmly implant the stent. Typically, the burst pressure of the outer balloon should be greater than that of the inner balloon. Thus, for example, in a particular embodiment the burst pressure of the inner balloon may be selected to be, for example, 5 atmospheres, and the burst pressure of the outer balloon may be selected to be equal to 10 atmospheres, i.e., to give an approximately 5 atmosphere difference.

The balloons may then be deflated, and the catheter and guidewire may then by removed.

In the foregoing specification, the invention has been described with reference to specific exemplary embodiments. It will, however, be evident that various modifications and changes may be made thereunto without departing from the broader spirit and scope of the invention as set forth in the appended claims. The specification and drawings are accordingly to be regarded in an illustrative rather than a restrictive sense.

What is claimed is:

1. A method of implanting a stent mounted on a balloon catheter with an outer balloon with an expanded length longer than the stent and an inner balloon with an expanded length shorter than the stent, the outer balloon overlaying the inner balloon, a burst pressure of the inner balloon being substantially less than a burst pressure of the outer balloon, said method comprising the steps of:
   delivering the balloon catheter and stent to a desired location in a vessel in a body;
   inflating the inner balloon to a pressure sufficient to expand initially a central portion of the stent only;
   continuing inflating the inner balloon to a pressure sufficient to burst the inner balloon;
   inflating the outer balloon to a pressure sufficient to implant the stent; and
   deflating and removing the balloon catheter.

2. The method according to claim 1, wherein the step of inflating the inner balloon to a pressure sufficient to expand a central portion of the stent implants the central portion of the stent and said step of inflating the outer balloon to a pressure sufficient to implant the stent implants the ends of the stent.

3. The method according to claim 2, wherein a burst pressure of the outer balloon is over approximately 10 atmospheres and a burst pressure of the inner balloon is less than approximately 5 atmospheres.

4. A method of implanting a stent mounted on a balloon catheter with an outer balloon with an expanded length longer than the stent and an inner balloon with an expanded length shorter than the stent, the outer balloon overlaying the inner balloon, said method comprising the steps of:
   delivering the balloon catheter and stent to a desired location in a vessel in a body;
   inflating the inner balloon to a pressure sufficient to expand the center portion of the stent only;
   continuing inflating the inner balloon to a pressure sufficient to burst the inner balloon;
   inflating the outer balloon to a pressure sufficient to implant the stent; and
   deflating and removing the balloon catheter.

5. The method according to claim 4, wherein the step of inflating the inner balloon to a pressure sufficient to expand the stent expands and implants the central portion of the stent and said step of inflating the outer balloon to a pressure sufficient to implant the stent implants the ends of the stent.

6. The method according to claim 4, wherein the pressure to burst the inner balloon is less than approximately 5 atmospheres.

7. A method of implanting a stent, comprising:
   expanding the central area of the stent with a first balloon, where the expanded length of the first balloon is shorter than the length of the stent;
   bursting the first balloon; and
   then expanding the ends of the stent with a second balloon, where the expanded length of the second balloon is longer than the length of the stent.

8. The method of claim 7 wherein said first balloon comprises an inner balloon disposed inside said second balloon comprising an outer balloon.

* * * * *